US012648861B2

(12) United States Patent
    Amanatullah

(10) Patent No.:    US 12,648,861 B2
(45) Date of Patent:        Jun. 9, 2026

(54) SYSTEM FOR IDENTIFYING POSITIONS OF AN ARTIFICIAL TIBIAL COMPONENT DURING TOTAL KNEE ARTHROPLASTY

(71) Applicant: Knimble Designs, Inc., Dover, DE (US)

(72) Inventor: Derek Amanatullah, Palo Alto, CA (US)

(73) Assignee: Knimble Designs, Inc., Menlo Park, CA (US)

( * ) Notice: Subject to any disclaimer, the term of this patent is extended or adjusted under 35 U.S.C. 154(b) by 57 days.

(21) Appl. No.: 18/755,524

(22) Filed: Jun. 26, 2024

(65) Prior Publication Data

US 2024/0423814 A1      Dec. 26, 2024

Related U.S. Application Data

(60) Provisional application No. 63/523,303, filed on Jun. 26, 2023.

(51) Int. Cl.
    *A61F 2/46*        (2006.01)
    *A61B 17/17*       (2006.01)
    *A61B 34/20*       (2016.01)
    *A61F 2/38*        (2006.01)

(52) U.S. Cl.
    CPC .......... *A61F 2/461* (2013.01); *A61B 17/1764* (2013.01); *A61B 34/20* (2016.02); *A61F 2/389* (2013.01); *A61F 2002/4633* (2013.01); *A61F 2002/4666* (2013.01)

(58) Field of Classification Search
    CPC . A61F 2/461; A61F 2/4657; A61B 2017/0268
    See application file for complete search history.

(56) References Cited

U.S. PATENT DOCUMENTS

| | | | | |
|---|---|---|---|---|
| 10,842,432 | B2 * | 11/2020 | Goodchild | .............. A61B 90/06 |
| 11,266,512 | B2 * | 3/2022 | Trabish | .................. A61B 5/107 |
| 2007/0239165 | A1 * | 10/2007 | Amirouche | .......... A61B 5/1121 |
| | | | | 606/86 R |
| 2015/0359642 | A1 * | 12/2015 | Claypool | .............. A61F 2/4657 |
| | | | | 623/20.32 |

\* cited by examiner

*Primary Examiner* — Andrew Yang

(57)                ABSTRACT

A system including a knee ranging tool: including a base configured to locate on a resected proximal face of a tibia in a knee of a patient; defining a tibial reference surface configured to run against a femoral surface of an artificial femoral component, installed on a distal face of a femur of the patient, during articulation of the knee of patient; including a set of stages interposed between the base and the tibial reference surface, configured to locate the tibial reference surface relative to the base, and compliant to medial-lateral translation, anteroposterior translation, and transverse rotation; and configured to indicate a medial-lateral translation offset, an anteroposterior translation offset, and a transverse rotation offset corresponding to a position of the tibial reference surface, relative to the base, that yields elastic deformation of ligaments in the knee over a range of motion of the knee.

19 Claims, 6 Drawing Sheets

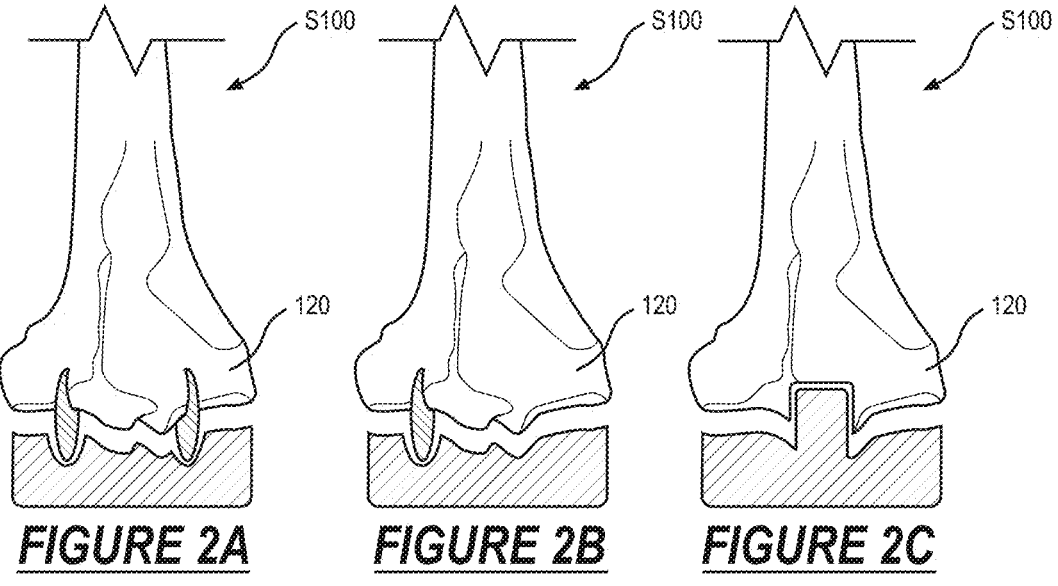
FIGURE 2A          FIGURE 2B          FIGURE 2C
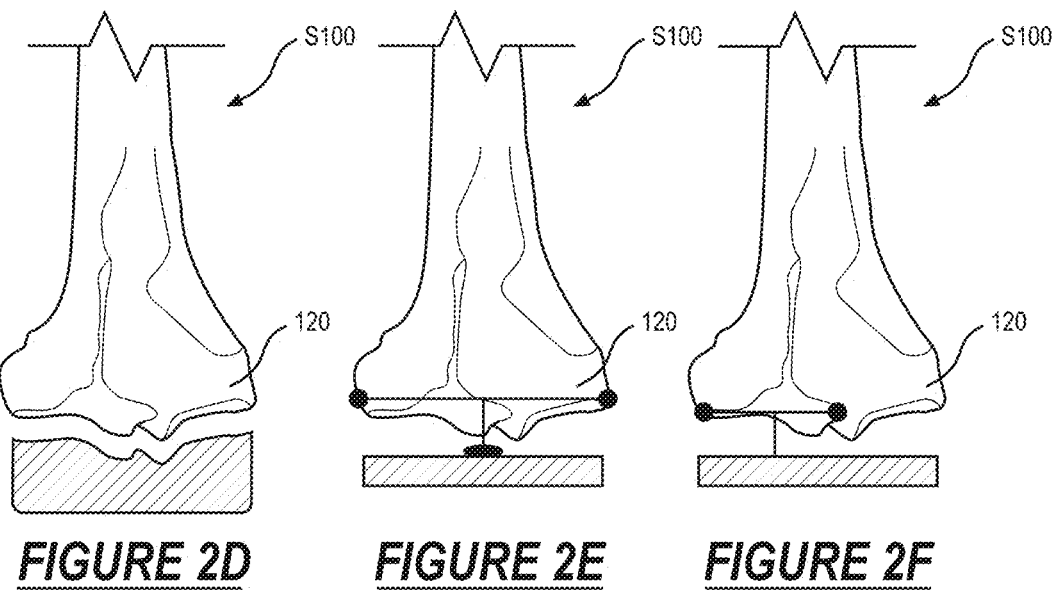
FIGURE 2D          FIGURE 2E          FIGURE 2F

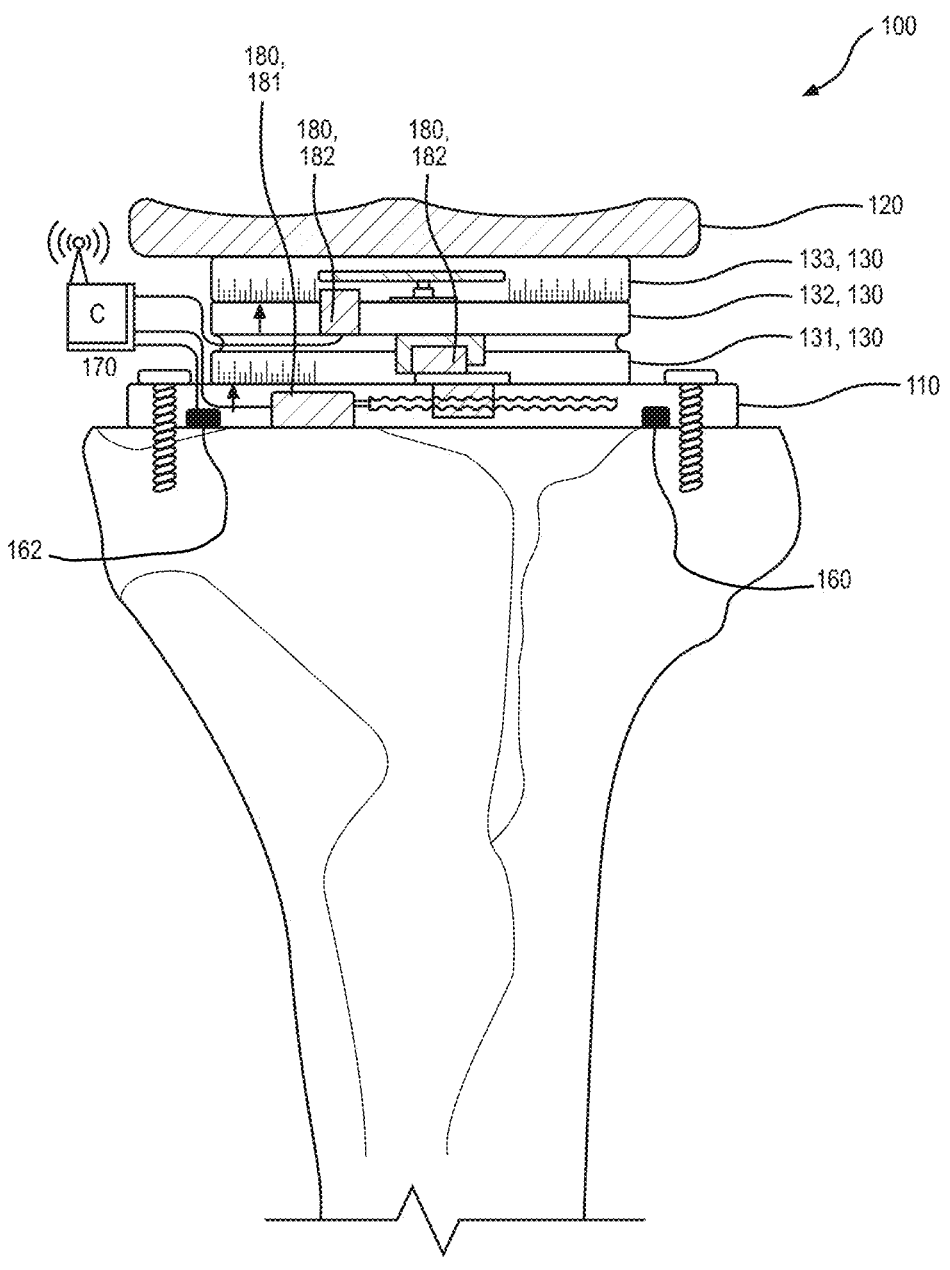
_FIGURE 4_

SYSTEM FOR IDENTIFYING POSITIONS OF AN ARTIFICIAL TIBIAL COMPONENT DURING TOTAL KNEE ARTHROPLASTY

CROSS-REFERENCE TO RELATED APPLICATIONS

This Application claims the benefit of U.S. Provisional Application No. 63/523,303, filed on 26 Jun. 2023, which is incorporated in its entirety by this reference.

This Application is related to U.S. Pat. Nos. 18,677,753 and 18,419,350, each of which is incorporated in its entirety by this reference.

TECHNICAL FIELD

This invention relates generally to the field of arthroplasty and more specifically to a new and useful system for total knee replacement in the field of arthroplasty.

BRIEF DESCRIPTION OF THE FIGURES

FIGS. 2A-2F are schematic representations of variations of the system;

FIG. 4 is a schematic representation of a variation of the system;

DESCRIPTION OF THE EMBODIMENTS

Figure 1:
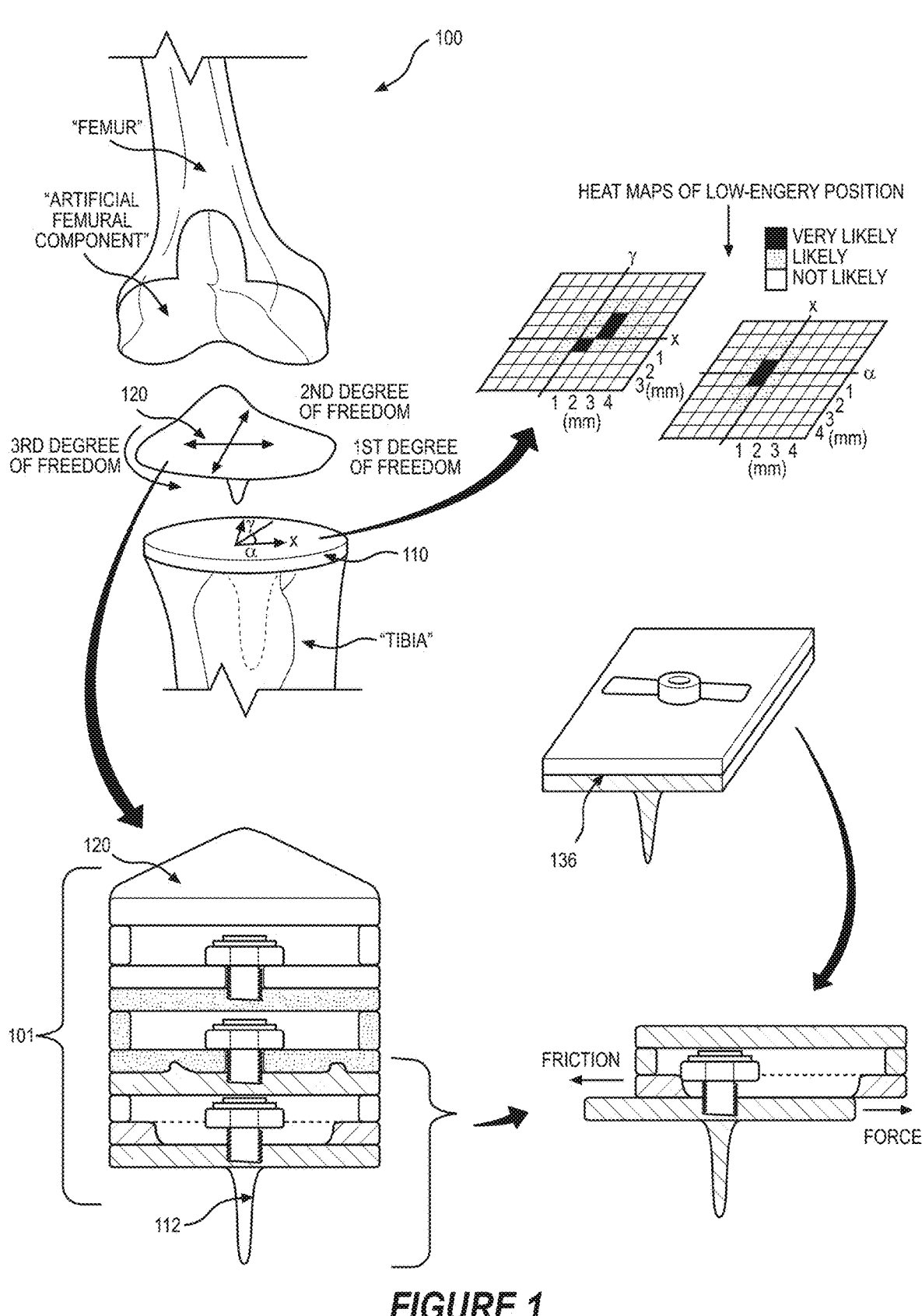
FIG. 1 is a flowchart representation of a system.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Stemless System

As shown in FIGS. 1-6, a system 100 includes a knee ranging tool 101: including a base 110 configured to transiently locate on a resected proximal face of a tibia in a knee of a patient; defining a tibial reference surface 120 configured to run against a femoral surface of an artificial femoral component, installed on a distal face of a femur of the patient, during articulation of the knee of patient; including a set of stages 130; and configured to indicate a medial-lateral translation offset, an anteroposterior translation offset, and a transverse rotation offset corresponding to a position of the tibial reference surface 120, relative to the base 110, that yields elastic deformation of ligaments in the knee over a range of motion of the knee. The set of stages 130 are: interposed between the base 110 and the tibial reference surface 120; configured to locate the tibial reference surface 120 relative to the base 110; and compliant to medial-lateral translation, anteroposterior translation, and transverse rotation.

1.1 Variation: Tibial Surface-Mount System

As shown in FIGS. 1 and 2A-2F, one variation of the system 100 includes: a base 110 configured to locate over (temporarily fasten to) a resected proximal end of a tibia of a patient; a temporary tibial component defining a temporary tibial surface configured to mesh with and slide against an artificial femoral component installed on a femur of the patient; and a set of stages 130. The set of stages 130 are: interposed between the base 110 and the temporary tibial component; and configured to constrain the temporary tibial component (relative to the base 110) in translation along a transverse axis of the base 110 and in rotation about a lateral axis and a sagittal axis of the base 110. The set of stages 130 are also: compliant to lateral translation of the temporary tibial component relative to the base 110 during articulation of a knee of the patient; compliant to sagittal translation of the temporary tibial component relative to the base 110 during articulation of the knee of the patient; compliant to angular rotation of the temporary tibial component about the transverse axis of the base 110 during articulation of the knee of the patient; and configured to lock against the base 110 in a final lateral position, sagittal position, and angular position of the temporary tibial component relative to the base 110 articulation of the knee of the patient.

1.2 Variation: Tibial Reaming Guide

Figure 3:
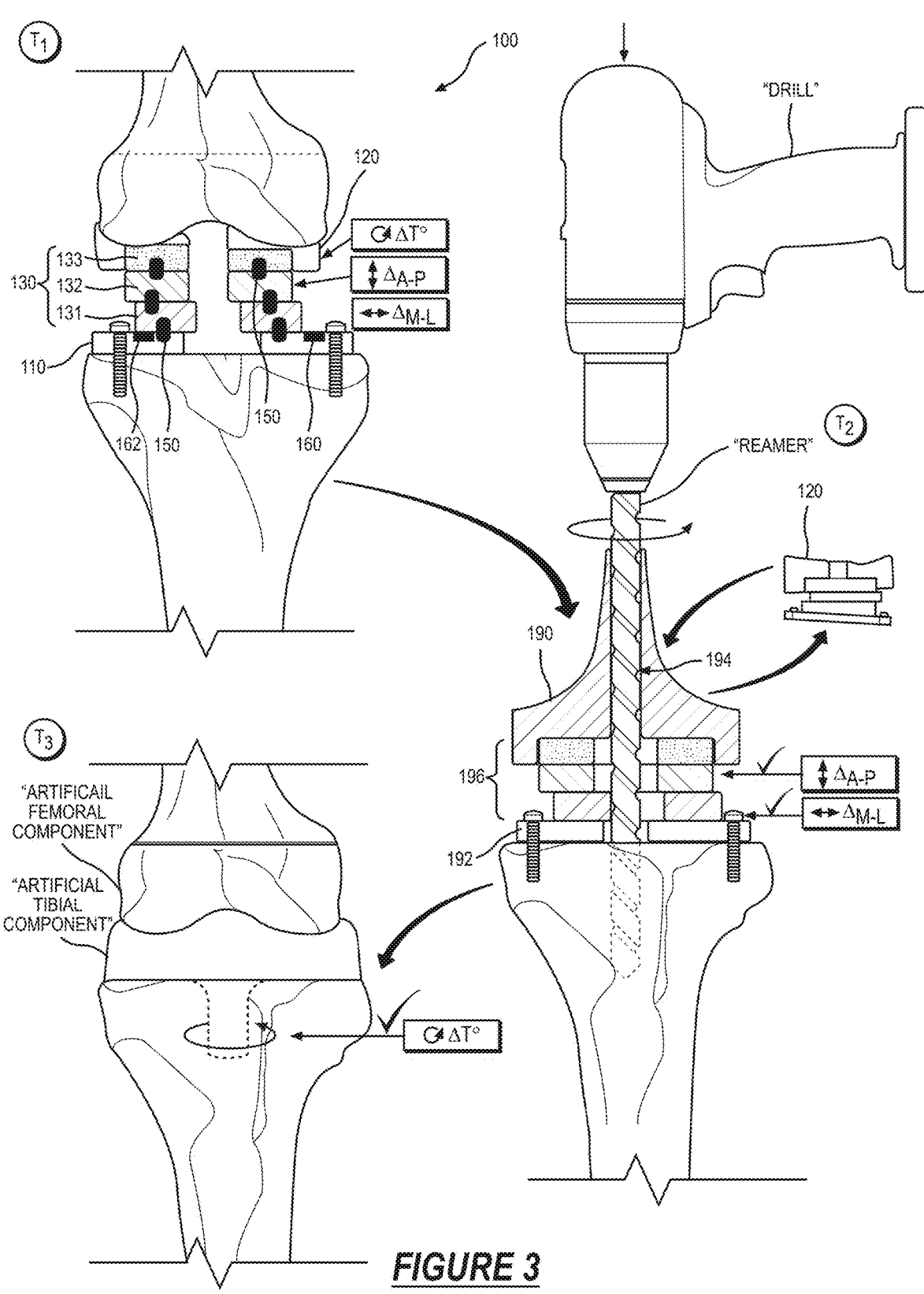
FIG. 3 is a flowchart representation of the system.
Figure 5:
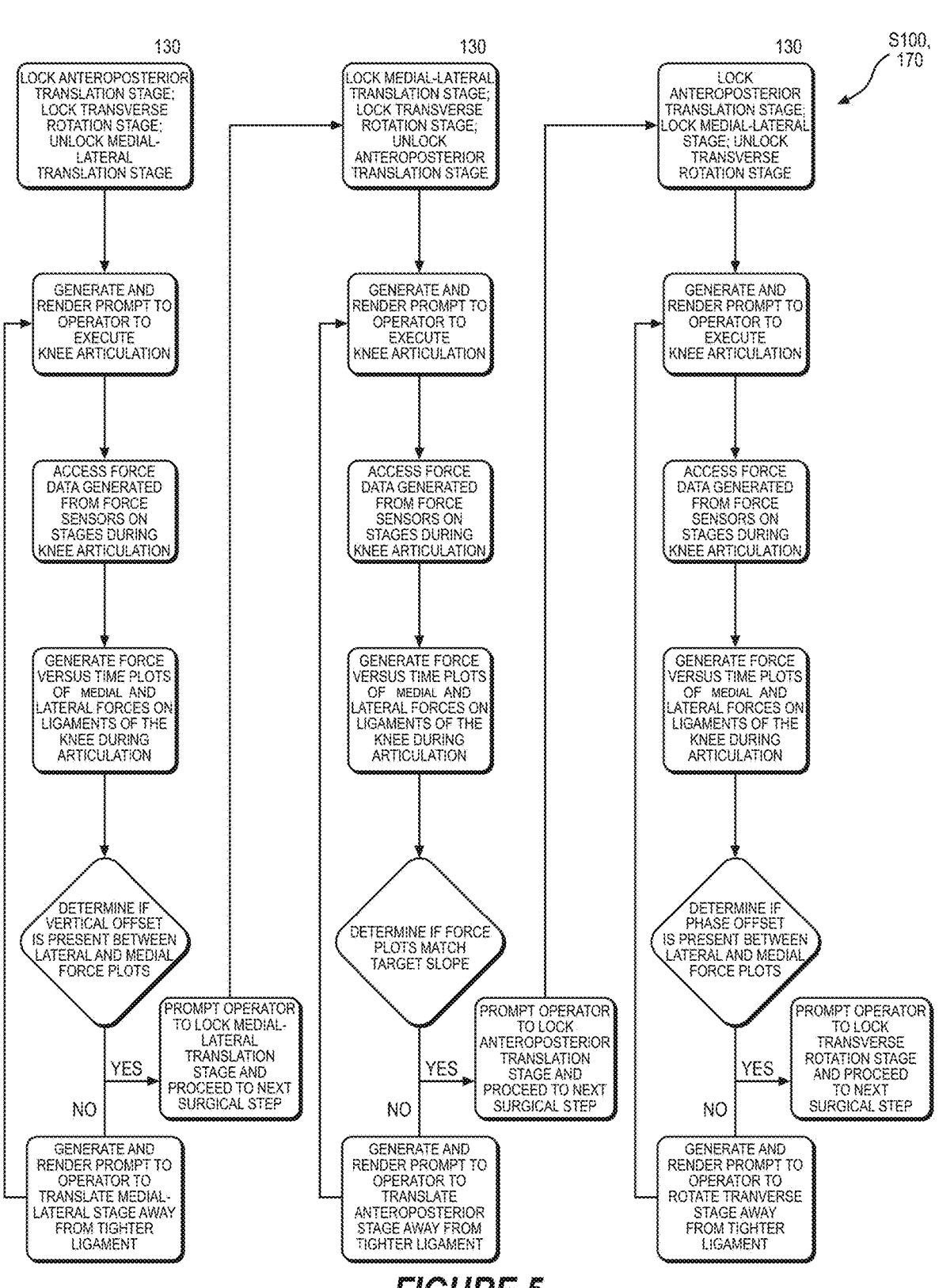
FIG. 5 is a flowchart representation of the system.
Figure 6:
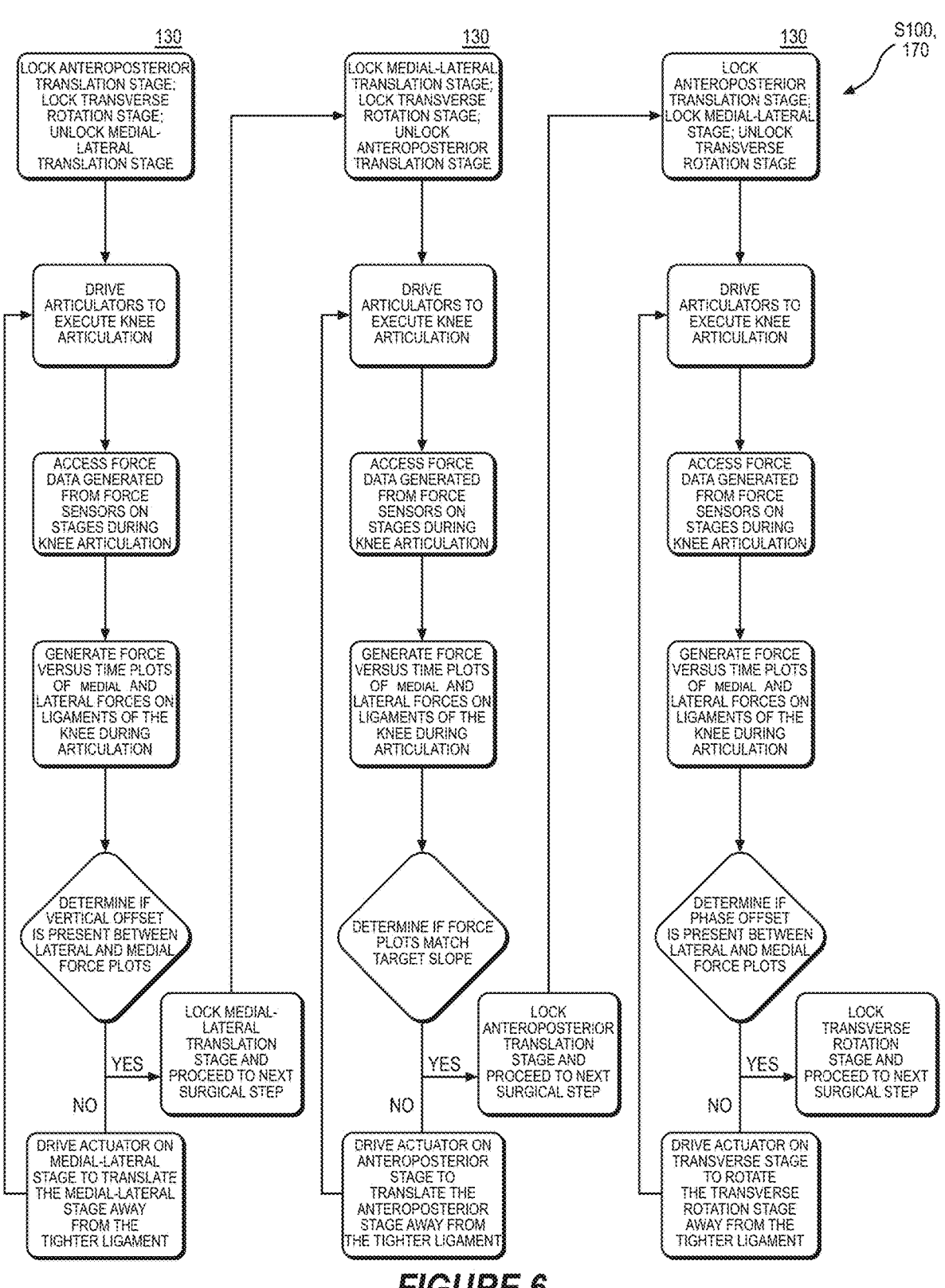
FIG. 6 is a flowchart representation of the system.

As shown in FIG. 3, one variation of the system 100 includes a knee ranging tool 101: including a base 110 configured to transiently locate on a resected proximal face of a tibia in a knee of a patient; defining a tibial reference surface 120 configured to run against a femoral surface of an artificial femoral component, installed on a distal face of a femur of the patient, during articulation of the knee of patient; including a set of stages 130; configured to indicate a medial-lateral translation offset and an anteroposterior translation offset corresponding to a position of the tibial reference surface 120, relative to the base 110, that yields elastic deformation of ligaments in the knee over a range of motion of the knee; and a reaming guide 194. The set of stages 130 are: interposed between the base 110 and the tibial reference surface 120; configured to locate the tibial reference surface 120 relative to the base 110; and compliant to medial-lateral translation, anteroposterior translation, and transverse rotation. The reaming guide 194 is: configured to transiently install on the tibia; adjustable over a range of medial-lateral translation and anteroposterior positions; and configured to locate a tibial reamer, during drilling of the tibia to receive a keel 112 of an artificial tibial component, according to the medial-lateral translation offset and the anteroposterior translation offset.

In this variation, the set of stages 130 includes: a first stage 131, a second stage 132, and a third stage 133. The first stage 131 is: compliant in medial-lateral translation; and configured to translate along a medial-lateral axis responsive to a first force component, along the medial-lateral axis, of a combined force applied by a medial-collateral ligament and a lateral-collateral ligament of the knee to the artificial femoral component and the tibia during articulation of the knee. The second stage 132 is: compliant in anteroposterior translation; and configured to translate along an anteroposterior axis responsive to a second force component, along the anteroposterior axis, of the combined force applied by the medial-collateral ligament and the lateral-collateral ligament during articulation of the knee. The third stage 133 is: compliant in transverse rotation; and configured to rotate about a transverse axis responsive to a torque, above the transverse axis, resulting from the combined force applied by the medial-collateral ligament and the lateral-collateral ligament during articulation of the knee.

In this variation, the system 100 also includes a tibial reamer guide configured to replace the temporary tibial component over the set of stages 130, located relative to the tibia by the base 110 and the set of stages 130, and configured to locate a reamer along a ream axis, relative to the temporary tibial surface, according to a geometry of a stem and a tibial surface of an artificial tibial component.

In this variation, during total knee arthroplasty, the surgeon: locates (temporarily fastens) the base 110 to the resected proximal end of the tibia; meshes the temporary tibial surface against the natural femoral condyle or artificial femoral component installed in the knee; moves the knee through range of motion, over which the set of stages 130 slip (i.e., translate laterally, translate sagittally, rotate transversely) against the base 110 to enable the temporary tibial surface to find a lowest-energy position in which the temporary tibial surface exhibits least binding with or impingement on the natural femoral condyle or artificial femoral component; locks the set of stages 130 in this lowest-energy position; replaces the temporary tibial component with the tibial reamer guide—that defines a ream axis relative to the temporary tibial surface that is analogous to a stem and tibial surface geometry of an artificial tibial component selected for the patient; reams the tibia via the tibial reamer guide; and installs the artificial tibial component in the patient's tibia.

1.3 Variation: Tibial Reaming Guide

In a similar variation, the base 110 is configured to locate on the resected face of the tibia via a set of laterally offset pins; and the system 100 further includes a tibial reaming tool 190. The tibial reaming tool 190 includes: a second base 192 configured to transiently locate on the resected proximal face of the tibia via the set of pins; a reaming guide 194 configured to locate a tibial reamer during drilling of the tibia to receive a keel 112 of an artificial tibial component; and a second set of stages 196. The second set of stages 196 is: interposed between the base 110 and the tibial reference surface 120; and configured to adjust in medial-lateral translation and anteroposterior translation according to the medial-lateral translation offset and the anteroposterior translation offset.

In this variation, the tibial reference surface 120 can be configured to transiently install on the set of stages 130. The set of stages 130 can be configured to lock at the medial-lateral translation offset and the anteroposterior translation offset, and the system 100 can further include a reaming guide 194 configured to transiently install on the set of stages 130, in replacement of the tibial reference surface 120, to locate a tibial reamer during drilling of the tibia to receive a keel 112 of an artificial tibial component.

1.4 Variation: Mechanical Position Indicators

In one variation, each stage in the set of stages 130 includes a set of indicators 136, the set of indicators 136 including: a first set of linear rule demarcations between a first stage 131 and the base 110; a second set of linear rule demarcations between a second stage 132 and the first stage 131; and a third set of angular rule demarcations between a third stage 133 and the second stage 132. In this variation, the set of indicators 136 are configured to: display the medial-lateral translation offset, the anteroposterior translation offset, and the transverse rotation offset of the tibial reference surface 120, relative to the base 110.

In another variation, the set of indicators 136 include a lateral scale, a sagittal scale, and a transverse angular scale arranged on the set of stages 130 and manually readable by a surgeon.

1.5 Variation: Position Sensors

In another variation, the system 100 can further include: a set of position sensors 150, each position sensor in the set of position sensors 150 configured to detect a position of a stage in the set of stages 130; and a controller 170. The controller 170 can be configured: to read the position of the stage from the position sensor; to output a medial-lateral position in the coronal plane of a first stage 131; to output an anteroposterior position in the sagittal of a second stage 132; and to output a rotational position in the transverse plane of a third stage 133.

In this variation, in the set of position sensors 150, each position sensor in the set of position sensors 150 is configured to output a position of a stage in the set of stages 130. The controller 170 can then: reduce the force output of a set of actuators 180 during sequential articulations of the knee; and implement a closed-loop control to maintain a first stage 131 in the set of stages 130 at a first position in response to the first position approximating a lowest-energy position of the stage in the set of stages 130.

In a similar variation, the set indicators includes a lateral linear position sensor, a sagittal linear position sensor, and a transverse angular position sensor coupled to the set of stages 130 and configured to output digital signals representing a lateral position, a sagittal position, and an angular position of the temporary tibial component relative to the stem. In this variation, the set of stages 130 are removable from the base 110 and the surgeon locates the tibial reamer guide on the base 110 according to the lateral position, the sagittal position, and the angular position of the temporary tibial component read from the set of position indicators 2. Stemmed System In one variation, the system 100 includes: a stem configured to insert into a bore in a tibia of a patient; a temporary tibial component defining a temporary tibial surface configured to mesh with and slide against a femoral component installed on a femur of the patient; and a set of stages 130 interposed between the stem and the temporary tibial component configured to constrain the temporary tibial component (relative to the stem) in translation along a transverse axis of the stem and in rotation about a lateral axis and a sagittal axis of the stem (e.g., the set of stages 130 prevent translation of the temporary tibial component along the transverse axis and rotation about the lateral axis and the sagittal axis). In this variation, the system 100 also includes a set of position indicators: configured to indicate a lateral position of the temporary tibial component relative to the stem, the temporary tibial component shifted laterally relative to the stem by the femoral component during articulation of a knee of the patient; configured to indicate a sagittal position of the temporary tibial component relative to the stem, the temporary tibial component shifted sagittally relative to the stem by the femoral component during articulation of the knee of the patient; and configured to indicate an angular position of the temporary tibial component about the transverse axis of the stem, the temporary tibial component rotated relative to the stem by the femoral component during articulation of the knee of the patient.

2.1 Variation: Stem Alternatives

In one variation, the system 100 includes a set of pins (e.g., instead of the stem) configured to temporarily fasten the temporary tibial component to the resected proximal end of the tibia. In another implementation, the system 100 includes a keel 112 (e.g., a blade) and/or a set of spikes extending from the set of stages 130 and configured to embed in the resected proximal end of tibia temporarily fixing the temporary tibial component to the tibia. In yet another implementation, the temporary tibial component is configured to temporarily fasten the resected proximal end of tibia due to a vertical force exerted on the temporary tibial surface by the artificial tibial component or the femoral condyle of the patient's femur. In this implementation, the temporary tibial component can include a high-friction distal surface configured to interface with the proximal end of the tibia and prevent the temporary tibial component from sliding relative to the tibia.

In this variation, the system 100 can further include a first keel 112: extending from a distal face of the base 110; and defining a geometry approximating a second keel 112 of an artificial tibial component, the artificial tibial component defining an artificial tibial surface. The first keel 112 is configured to: insert into a reamed bore in the tibia; and locate the base 110 relative to the reamed bore in the tibia. In this example, the set of stages 130 are configured to indicate: the anteroposterior translation offset that corresponds to an anteroposterior position of the artificial tibial surface relative to the second keel 112 on the artificial tibial component; the medial-lateral translation offset that corresponds to a medial-lateral position of the artificial tibial surface relative to the second keel 112 on the artificial tibial component; and the transverse rotation offset that corresponds to a transverse position of the artificial tibial surface relative to the second keel 112 on the artificial tibial component.

2.2 Variation: Position Indicators

In one variation, the set of indicators 136 includes lateral scale, sagittal scale, and transverse angular scale arranged on the set of stages 130 and manually readable by a surgeon.

In another variation, the set of indicators 136 include a lateral linear position sensor, a sagittal linear position sensor, and a transverse angular position sensor coupled to the set of stages 130 and configured to: output digital signals representing lateral position, sagittal position, and angular position of the temporary tibial component relative to the stem. In this variation, the system 100 further includes a wired or wireless communication module configured to transmit digital signals.

2.3 Variation: Prefabricated Artificial Components

In one variation, the system 100 further includes (or is paired with) a set of prefabricated artificial tibial components, each artificial tibial component in the set of prefabricated artificial tibial components: including a stem; including a tibial surface laterally, sagittally, and transverse angularly offset from the stem by a unique geometry within the set of prefabricated artificial tibial components; and selectable by a surgeon, for installation in the patient's tibia, based on proximity of the unique geometry to the lateral position, the sagittal position, and the angular position of the temporary tibial component relative to the stem read from the set of position indicators following articulation of the knee of the patient.

In this variation, the surgeon: locates (temporarily fastens) the stem in a pre-reamed bore in the proximal end of the tibia during total knee arthroplasty; meshes the temporary tibial surface against the natural femoral condyle or the artificial femoral component installed in the knee; moves the knee through range of motion, over which the set of stages 130 slip (i.e., translate laterally, translate sagittally, rotate transversely) against the base 110 to enable the temporary tibial surface to find a lowest-energy position in which the temporary tibial surface exhibits least binding with or impingement on the natural femoral condyle or the artificial femoral component; reads positions from the set of position indicators; retrieves a prefabricated artificial tibial component—from a suite or library of prefabricated artificial tibial components of various geometries—defining a geometry that most closely corresponds to these positions; and installs this prefabricated artificial tibial component in the patient's tibia.

3. Applications

Generally, the system 100 is configured to aid a surgeon in installing an artificial tibial component on a patient's tibia during knee arthroplasty. The system 100 includes: a temporary tibial component temporarily installed on the proximal end of a patient's tibia and configured to interface with an artificial femoral component or a femoral condyle of a patient's femur; a set of stages 130 configured to enable translation and/or rotation of the temporary tibial component relative to the tibia; and a set of position indicators configured to indicate positions of the temporary tibial component. The system 100 is configured to: enable translation and/or rotation of a temporary tibial component in three degrees of freedom (of the temporary tibial component) relative to the tibia in response to articulation of a patient's knee through a range of motion during knee arthroplasty; and indicate positions (e.g., lateral position, sagittal position, and transverse rotation, hereinafter "$\{x, y, a\}$") of the temporary tibial component. In particular, during articulation of the knee through a range of motion, the temporary tibial component of the system 100 may enter a low-energy position in which the temporary tibial surface exhibits impingement on the artificial femoral component or the natural femoral condyle. Following articulation of the knee through the range of motion, the surgeon may read the coordinates, $\{x', y', a'\}$, associated with the low-energy position from the position indicators of the system, and select from a suite of prefabricated artificial tibial components of various geometries, an artificial tibial component defining a geometry that most closely corresponds to the low-energy position indicated by the system. Additionally, or alternatively, following articulation of the knee through the range of motion, the surgeon may: replace the temporary tibial component with a tibial reamer guide defining a ream axis analogous to a stem and a tibial surface geometry of an artificial tibial component positioned in the low-energy position; ream the tibia via the tibial reamer guide; and install the artificial tibial component in the low-energy position.

In one implementation, the system 100 is configured to constrain translation or rotation of the temporary tibial component in one or more degrees of freedom. In particular, each stage in the set of stages 130 is configured to lock, thereby constraining movement of the temporary tibial component in one degree of freedom. Thus, prior to articulating the knee through a range of motion, the surgeon may lock (i.e., constrain) a first stage 131 of the set of stages 130 to prevent the first stage 131 from reaching a limit of its translational range. Conversely, prior to articulating the knee through the range of motion, the surgeon my unlock (i.e., unconstrain) a second stage 132 of the set of stages 130 to enable the second stage 132 to translate or rotate into the low-energy position.

In one example, during a knee arthroplasty, a surgeon may: install an artificial femoral component on the distal end of the femur; resect a proximal end of the patient's tibia; and install the base 110, the set of stages 130, and the temporary tibial component on the resected tibial surface. During this process, the surgeon may use guides and tension tools, as described in U.S. patent application Ser. No. 17/515,205, to ensure that tensions on the MCL and LCL are accurately reproduced when the artificial femoral component and the temporary tibial component are implanted in the patient. Alternatively, the surgeon may forgo installing the artificial femoral component on the patient's femur prior to installing the temporary tibial component and the artificial tibial component.

In this example, at a first time, the surgeon may unconstrain the temporary tibial component in a first degree of freedom (e.g., lateral translation), in a set of three degrees of freedom (e.g., lateral translation, sagittal translation, transverse rotation) of the temporary tibial component; and manipulate the knee through a range of motion, while the temporary tibial component moves in a first degree of freedom. The surgeon may repeat the process of unconstraining (or "releasing") the temporary tibial component in one degree of freedom and manipulating the knee though a range of motion at a second time and at a third time. At a second time, the surgeon may unconstrain a second degree of freedom (e.g., sagittal translation) of the temporary tibial component and, at a third time, the surgeon may unconstrain the third degree of freedom (e.g., transverse rotation) of the temporary tibial component. The surgeon then may read the positions output by the position indicators and identify the target positions (e.g., low-energy positions) of the artificial tibial component relative to the tibia.

Upon identifying the target positions of the artificial tibial component, the surgeon may utilize a tibial reamer guide to permanently install the artificial tibial component at the target positions on the tibia and complete the knee arthroplasty. The artificial tibial component installed at the target position can help maintain balanced ligament tensions in the knee. Accordingly, the patient may perceive balanced soft tissue tensions in her artificial knee joint over its range of motion following recovery from the surgery—that is, sufficient ligament tension to avoid a sense of "imbalance," "tightness," or "looseness."

4. Artificial Knee Components

Generally, an artificial knee joint can include: an artificial femoral component installed on a distal end of a patient's femur; and an artificial tibial component installed on a proximal end of the patient's tibia and configured to form a joint with the artificial femoral component.

The artificial femoral component defines an internal posterior face, an internal anterior face, and an internal proximal face configured to mate with the anterior femoral face, the distal femoral face, and the posterior femoral face resulting from an anterior femoral cut, a distal femoral cut, and a posterior femoral cut on the femur performed by the surgeon. The artificial femoral component also defines an external distal surface configured to interface with the artificial tibial component. For example, the external distal surface of the artificial femoral component can include two condyles configured to interface (form a joint with) with a ridge in the articulating proximal surface of the artificial tibial component. For example, the tibial reference surface 120 can approximate a geometry of a condyle of an artificial tibial component selected for installation on the tibia of the patient. In a similar example, the tibial reference surface 120 can include a set of grooves configured to run along a set of condyles of the artificial femoral component during articulation of the knee, as shown in FIGS. 2A-2F.

The system is described herein as including a knee ranging tool 101 defining a tibial reference surface decoupled from (i.e., not pinned to or hinged to a fixed axis of rotation of) an artificial femoral component. However, in one variation, the knee ranging tool 101 is configured to transiently hinge to or otherwise couple to the artificial femoral component. For example, the knee ranging tool 101 can include a hinge: arranged over the set of stages opposite the base; and configured to temporarily pivot against the artificial femoral component about a fixed pivot axis. During a surgical operation: the knee ranging tool 101 can be located on the resected proximal end of the tibia; the artificial femoral component can be located on the resected distal end of the femur and temporally hinged to the proximal end of the knee ranging tool 101; and the knee can be articulated through flexion and extension, which can drive the set of stages to low-energy positions on the base that correspond to minimum and/or balanced tensions on the medial and lateral ligaments of the knee. The surgeon may then: read position indicators from the stages; remove the knee ranging tool 101 from the tibia; and replicate these position indicators when finalizing placement of the artificial tibial component on the tibia, as described below.

The artificial tibial component can include a tibial plate defining a distal face that mates to the proximal tibial face, the proximal tibial face resulting from a tibial cut on the proximal end of the tibia. The artificial tibial component can also include a tibial stem extending from the distal face of the tibial plate and configured to insert into a tibial bore.

In one variation, the system 100 includes a set of prefabricated artificial tibial components, each artificial tibial component defining a unique geometry. In particular, each artificial tibial component in the set of prefabricated artificial tibial components can include: a stem configured to insert into a tibial bore; and a tibial surface laterally, sagittally, and transverse angularly offset from the stem by a unique geometry within the set of artificial tibial components. A surgeon may select a particular artificial tibial component in the set of prefabricated artificial tibial components for installation in the patient's tibia, based on proximity of the unique geometry of the particular artificial tibial component to a lateral position, a sagittal position, and an angular position read from the set of position indicators following articulation of the knee of the patient.

5. Temporary Tibial Component

Prior to installing the artificial tibial component, the surgeon may temporarily install the system 100 (e.g., temporary tibial component, the set of stages 130, the base 110/stem) as part of the knee joint and, based on the position indicators of the temporary tibial component, identify the target positions of the artificial tibial component that maintain balanced tensions of the MCL and the LCL.

In one implementation, the system 100 can include: a stem configured to insert into a bore in a tibia of a patient; a temporary tibial component defining a temporary tibial surface configured to mesh with and slide against an artificial femoral component installed on a femur of the patient; and a set of stages 130 interposed between the stem and the temporary tibial component and configured to constrain the temporary tibial component relative to the stem, the set of stages 130 in translation along a transverse axis of the stem and in rotation about a lateral axis and a sagittal axis of the stem. Therefore, the stem can be fixed on the tibia and the set of stages 130 can enable the temporary tibial component to move in three degrees of freedom relative to the stem.

5.1 Mechanical Position Indicators

In one implementation, the system 100 also includes a set of position indicators: configured to indicate a lateral position of the temporary tibial component relative to the stem, the temporary tibial component shifted laterally relative to the stem by the femoral component during articulation of a knee of the patient; configured to indicate a sagittal position of the temporary tibial component relative to the stem, the temporary tibial component shifted sagittally relative to the stem by the femoral component during articulation of the knee of the patient; and configured to indicate an angular position of the temporary tibial component about the transverse axis of the stem, the temporary tibial component rotated relative to the stem by the femoral component during articulation of the knee of the patient. Therefore, the set of position indicators can output the positions, {x, y, a}, of the temporary tibial component relative to the stem following articulation of the knee of the patient.

For example, the set of position indicators include lateral scale, sagittal scale, and transverse angular scale arranged on the set of stages 130 and manually readable by a surgeon.

5.2 Position Sensors

In another implementation, the set of indicators 136 includes a lateral linear position sensor, a sagittal linear position sensor, and a transverse angular position sensor coupled to the set of stages 130 and configured to output digital signals representing a lateral position, a sagittal position, and an angular position of the temporary tibial component relative to the stem. For example, the lateral linear position sensor and sagittal linear position sensor can include linear encoders configured to output digital signals representing lateral displacement, and sagittal displacement of the temporary tibial component relative to the stem. The transverse angular sensor can include a rotary encoder configured to output digital position signals representing angular displacement of the temporary tibial component relative to the stem.

In this implementation, the system 100 further includes a wired or wireless communication module configured to transmit digital position signals. In this implementation, the wired or wireless communication module can transmit a series of lateral positions, sagittal positions, and angular positions of the temporary tibial component to an external controller 170 configured to display the current lateral position, sagittal position, and angular position of the temporary tibial component in real time. Therefore, the external controller 170 can dynamically track the positions of the temporary tibial component relative to the tibia. In this implementation, the external controller 170 can further generate a visual representation of the movement of the temporary tibial component relative to the tibia based on the series of lateral positions, sagittal positions, and angular positions in real time and transmit the visual representation to a display for viewing by the surgeon.

In one example, following the knee articulation performed by the surgeon, the wired or wireless communication module can transmit lateral position, sagittal position, and angular position of the temporary tibial component to an external controller 170. Based on the series of lateral position, sagittal position, and angular position measurements and based on the known topology of the tibial surface of the temporary tibial component, the external controller 170 can generate a three-dimensional model of the temporary tibial component; and transmit the three-dimensional model of the temporary tibial component to a 3D printer for printing. Therefore, the artificial tibial component can include a 3D-printed artificial tibial component model based on the lateral position, sagittal position, and angular position measurements and based on the known topology of the tibial surface of the temporary tibial component. Accordingly, instead of selecting an artificial tibial component in a set of artificial tibial components, a surgeon may install a custom-made (e.g., 3D printed) artificial tibial component.

5.3 Force Sensors

In one variation, the system 100 can further include a medial force sensor 160, a lateral force sensor 162, and a controller 170. The medial force sensor 160: is coupled to the set of stages 130; and is configured to output a first series of medial force values representing tension on a medial ligament of the knee. The lateral force sensor 162 is: coupled to the set of stages 130; laterally offset from the medial force sensor 160; and configured to output a second series of lateral force values representing tension on a lateral ligament of the knee. The controller 170 is configured to: characterize a difference between concurrent tensions on the medial ligament and tensions on the lateral ligament based on the first series of medial force values and the second first series of lateral force values; and scan the first series of medial force values for a first indication of inelastic deformation of the medial ligament.

In response to convergence of the first series of medial force values and the second series of lateral force values toward minimum forces during articulation of the knee and the difference exceeding a threshold difference, the controller 170 can generate a first prompt to adjust a medial-lateral position of the artificial femoral component on the distal face of the femur. In response to convergence of the first series of medial force values and the second series of lateral force values toward minimum forces during articulation of the knee and absence of the first indication of inelastic deformation of the medial ligament in the first series of medial force values, the controller 170 can: generate a second prompt to locate an artificial tibial component on the tibia according to the medial-lateral translation offset, the anteroposterior translation offset, and the transverse rotation offset indicated by the set of stages 130.

In this variation, the controller 170 can be further configured to: generate a third prompt to adjust the set of stages 130 to displace the tibial reference surface 120, relative to the base 110, toward the lateral ligament in response to presence of the first indication of inelastic deformation of the medial ligament in the first series of medial force values; and generate a fourth prompt to adjust the set of stages 130 to reposition the tibial reference surface 120 on the base 110 in response to absence of convergence of the first series of medial force values and the second series of lateral force values toward minimum forces during articulation of the knee.

In a similar implementation, the system 100 can further include: a medial force sensor 160 and a lateral force sensor 162. The medial force sensor 160 is: coupled to the set of stages 130; and configured to output a first series of medial force values representing tension on a medial ligament of the knee. The lateral force sensor 162 is: coupled to the set of stages 130; laterally offset from the medial force sensor 160; and configured to output a second series of lateral force values representing tension on a lateral ligament of the knee. In this implementation, the set of stages 130 includes manually operable set position controls and are configured to: translate in response to surgeon input during surgery; transiently lock in place in response to surgeon input during surgery during articulation of the knee through the range of motion; and transiently unlock in response to surgeon input in response to the force sensor output deviating from a target force in the range of motion indicating a balanced and elastic position of the tibial reference surface 120 with respect to the artificial femoral component.

Therefore, in this variation, the system 100 can include a force sensor interposed between the temporary tibial surface and the set of stages 130 and configured to indicate the vertical force exerted on the temporary tibial surface by the artificial femoral component or the natural femoral condyle of the patient's femur. In this implementation, the force sensor can output digital force readings representing the vertical force on the temporary tibial surface. In this variation, the wired or wireless communication module can transmit a series of digital force readings to the external controller 170 configured to display the series of digital force readings on a display for viewing by the surgeon. In this implementation, the surgeon may: read the series of digital force readings while moving the patient's knee through range of motion; based on the series of digital force readings, determine that the vertical force exerted on the temporary tibial surface by the artificial femoral component or the femoral condyles of the patient's femur is high leading to possible tightness and/or reduced range of motion of the patient's knee; and, in response to determining that the vertical force is high, further resect the tibia creating a second proximal tibial surface.

In this variation, the system 100 further includes (or is paired with) a set of prefabricated artificial tibial components, each artificial tibial component in the set of prefabricated artificial tibial components: including a stem; including a tibial surface laterally, sagittally, transverse angularly, and/or vertically offset from the stem by a unique geometry within the set of prefabricated artificial tibial components; and selectable by a surgeon, for installation in the patient's tibia. In this implementation, the surgeon may select a prefabricated artificial tibial component from the set of prefabricated artificial tibial components based on: the vertical force read from the force sensor; and proximity of the unique geometry to the lateral position, the sagittal position, and the angular position of the temporary tibial component read from the set of position indicators following articulation of the knee of the patient.

For example, the surgeon may: read a series of digital force readings output by the force sensor while moving the patient's knee through range of motion; and, based on the series of digital force readings, determine that the vertical force exerted on the temporary tibial surface by the artificial femoral component or the femoral condyles of the patient's femur is low leading to a possible imbalance of tensions of the medial collateral ligament and the lateral collateral ligament in the patient's knee. Then, the surgeon may: select a prefabricated artificial tibial component from the set of prefabricated artificial tibial components, the prefabricated artificial tibial component including an unique geometry where the vertical offset of the tibial surface from the stem exceeds the vertical dimension (e.g., height) of the temporary tibial component.

6. Surgical Operation

During a knee arthroplasty, a surgeon may: open a patient's soft tissue around her knee to expose the distal end of the patient's femur and the proximal end of the patient's tibia. The surgeon may then perform a series of bony cuts to resect several portions of the distal end of the patient's femur and install the artificial femoral component on the distal end of the patient's femur. In particular, the surgeon may use guides, prefabricated artificial femoral components, and a tension tool to: quantify relationships between force and ligament strain in a knee over a range of motion; account for ligament tension when performing bony cuts; and thus accurately and repeatably yield collateral ligaments tensed according to the surgeon's specified targets (e.g., equally-tensed) over the range of motion of the patient's knee, as described in U.S. patent application Ser. No. 17/515,205. Alternatively, the surgeon may forgo installing the artificial femoral component. The surgeon may also utilize the guides and the tension tool to: resect a proximal portion of the patient's tibia to create a proximal tibial surface; and to perform a tibial bore cut to create the tibial bore, as described in U.S. patent application Ser. No. 17/515,205.

6.1 Simultaneous Knee Balancing

In one variation, each stage in the set of stages 130 of the system 100 can be coupled to a clutch providing sliding friction between the stages. In this variation, the surgeon may install the system 100 including the temporary tibial component and the set of stages 130 on the resected tibia of the patient by: locating (temporarily fastening) the stem in the pre-reamed bore in the proximal end of tibia and meshing a temporary tibial surface of the temporary tibial component against the natural femoral condyle or the artificial femoral component installed in knee. In one implementation, the surgeon may configure the system 100 such that the initial position of the temporary tibial component is the reference position, {x, y, a}={0, 0, 0}. Therefore, the surgeon can temporarily install the system 100 on the tibia and configure the temporary tibial component to slide relative to the tibia in response to receiving forces exerted by the artificial femoral component during articulation of the knee through various ranges of motion.

The surgeon may then move the knee through a range of motion in three degrees of freedom (e.g., flexion-extension, external-internal rotation, varus-valgus rotation) of the knee. In response to the movement of the knee in three degrees of freedom, one or more stages in the set of stages 130 can translate (e.g., lateral translation, sagittal translation) or rotate (e.g., transverse rotation) relative to the stem to enable the temporary tibial surface to move to a lowest-energy position in which the temporary tibial surface exhibits least impingement (i.e., least amount of force exerted) on the natural femoral condyle or the artificial femoral component. Therefore, the temporary tibial component is configured to move to a position in which forces exerted on the temporary tibial component by the artificial femoral component and the medial collateral ligament and the lateral collateral ligament are balanced in various configurations of the knee.

The surgeon may then read final positions, {x, y, a}={x', y', a'}, from a set of position indicators of the system. The surgeon may then retrieve a prefabricated artificial tibial component—from a suite or library of prefabricated artificial tibial components of various geometries—defining a geometry that most closely corresponds to the final position; and install this prefabricated artificial tibial component in the patient's tibia. Therefore, the surgeon may select a prefabricated artificial tibial component that matches the geometry of the system 100 in the final position. Accordingly, the surgeon may install on the tibia the prefabricated artificial tibial component that minimizes impingement with the artificial femoral component and yields balanced tensions on the lateral collateral ligament and the medial collateral ligament.

6.2 Sequential Knee Balancing

In one variation, each stage in the set of stages 130 can be coupled to a latch enabling the stage to lock, thereby constraining movement of the temporary tibial component in one degree of freedom. Prior to articulating the knee through a motion in the first degree of freedom, the surgeon may lock a first stage 131 associated with translation in the first degree of freedom to prevent the first stage 131 from reaching a limit of a translational range. For example, the surgeon may lock the stage associated with lateral translation prior to articulating the patient's knee through varus-valgus rotation, as the varus-valgus rotation of the knee applies lateral force to the temporary tibial component and causes lateral translation of the stages and the temporary tibial component. Additionally, prior to articulating the knee through a motion in two degrees of freedom, the surgeon may lock two stages of the set of stages 130 to prevent the two stages from reaching their respective translational limits. For example, the surgeon may lock the stages associated with sagittal translation and transverse rotation prior to articulating the patient's knee through a motion including internal-external rotation and flexion-extension, as this motion applies sagittal force and transverse angular force to the set of stages 130 and the temporary tibial component and causes sagittal translation and transverse rotation of the temporary tibial component.

In one example, after installing the set of stages 130 and the temporary tibial component on the patient's tibia, during a first time period, the surgeon may unlock a first stage 131 of the set of stages 130 (while keeping the other stages locked). By unlocking a first stage 131, the surgeon may unlock movement of the temporary tibial component in a first degree of freedom (i.e., lateral translation), of the set of three possible degrees of freedom (e.g., lateral translation, sagittal translation, rotation about the transverse axis) of the set of stages 130. The surgeon may then articulate the knee through a first range of motion including flexion-extension and external-internal rotation of the knee. Following articulation of the knee through a first range of motion, the surgeon may record the final position, {x'}, output by a position indicator associated with the first stage 131.

During a second time period, the surgeon may unlock a second stage 132 of the set of stages 130 enabling movement of the temporary tibial component in a second degree of freedom (e.g., sagittal translation). The surgeon may then articulate the knee through a second range of motion including internal-external rotation and varus-valgus rotation of the knee. Following the articulation of the knee through a second range of motion, the surgeon may record the final position, {y'}, output by a position indicator associated with the second stage 132.

During a third time period, the surgeon may unlock a third stage 133 of the set of stages 130 enabling movement of the temporary tibial component in a third degree of freedom (e.g., angular rotation about the transverse axis). The surgeon may articulate the knee through a third range of motion including flexion-extension and varus-valgus rotation. Following the articulation of the knee through a second range of motion, the surgeon may record the final angular position, {a'}, of the temporary tibial component. In one implementation, the surgeon may measure the final positions of the temporary tibial component simultaneously during the third time.

Accordingly, the system 100 is configured to lock in select degrees of freedom, thereby preventing individual stages in the set of stages 130 from reaching their respective translational or rotational limits. Therefore, in response to articulation of the knee through several ranges of motion, the temporary tibial component can move to a position within an area defined by the resected tibial surface, the position in which the forces exerted on the temporary tibial component by the artificial femoral component are minimized.

6.3 Surgical Operation with Tibial Reamer Guide

In one variation, the system 100 can include a tibial reamer guide configured to replace the temporary tibial component over the set of stages 130 located relative to the tibia by the base 110 and the set of stages 130 and configured to locate a reamer along a ream axis, relative to the temporary tibial surface, according to a geometry of a stem and a tibial surface of an artificial tibial component.

In this variation, after installing the artificial femoral component on the femur, the surgeon may utilize the guides and the tension tool to: resect a proximal portion of the patient's tibia, as described in U.S. patent application Ser.

No. 17/515,205. The surgeon may then locate (temporarily fasten) a base 110 (e.g., base 110 of the system) to resect the proximal end of the tibia and mesh the temporary tibial surface against the natural femoral condyle or the artificial femoral component installed in the knee.

The surgeon may then: move the knee through a range of motion, over which the set of stages 130 slip (i.e., translate laterally, translate sagittally, rotate transversely) against the base 110 to enable the temporary tibial surface to find a lowest-energy position in which the temporary tibial surface exhibits least impingement on the natural femoral condyle or artificial femoral component; and locks the set of stages 130 in this lowest-energy position.

The surgeon may then replace the temporary tibial component with the tibial reamer guide—that defines a ream axis relative to the temporary tibial surface that is analogous to a stem and tibial surface geometry of an artificial tibial component selected for the patient, ream the tibia via the tibial reamer guide, and install the artificial tibial component in the patient's tibia. In particular, the surgeon may ream the tibia to create a tibial bore. Therefore, after identifying a lowest-energy position in which the temporary tibial surface exhibits least impingement on the natural femoral condyle or artificial femoral component, the surgeon may utilize the tibial reamer guide to install an artificial tibial component at the lowest-energy position such that impingement on the natural femoral condyle or artificial femoral component is reduced.

7. Force-Based Feedback: Force v. Time Plots

As described above, the system 100 can include a first (e.g., medial) force sensor, a second (e.g., lateral) force sensor, and a controller 170. In this variation, the first force sensor is: coupled to the set of stages 130; and configured to output a first series of force values representing tension on a medial-collateral ligament of the knee. The second force sensor is: coupled to the set of stages 130; and configured to output a second series of force values representing tension on a lateral-collateral ligament of the knee. The controller 170 is configured to: generate a medial force versus time plot representing tensile forces on the medial-collateral ligament over time during articulation of the knee, based on the first series of force values; generate a lateral force-versus-time plot, representing tensile forces on the lateral-collateral ligament over time during articulation of the knee, based on the second series of force values; and, in response to the medial force versus time plot approximating the lateral force versus time plot, generate a first prompt to locate an artificial tibial component on the tibia according to the medial-lateral translation offset, the anteroposterior translation offset, and the transverse rotation offset indicated by the set of stages 130.

The controller 170 can also: generate a second prompt to rotate the reference surface about a transverse axis of the knee via the set of stages 130 in response to detecting a phase offset between the medial force-versus-time plot and the lateral force-versus-time plot; generate a third prompt to translate the reference surface along a medial-lateral axis of the knee via the set of stages 130 in response to detecting a vertical offset between the medial force-versus-time plot and the lateral force-versus-time plot; derive a slope of the medial force versus time plot; and generate a fourth prompt to translate the reference surface, along an anteroposterior axis of the knee via the set of stages 130 in response to the slope of the medial force-versus-time plot falling outside of a target slope range.

For example, the controller 170 can generate or output a force versus time plot representing a change in medial or lateral force exerted on a medial or lateral knee of the patient during articulation of the knee. When the medial and lateral force plots converge on a similar (e.g., exact) shape, the controller 170 can output a prompt instructing a surgeon to proceed to the following surgical step, such as locating an artificial tibial component on the tibia according to the medial-lateral translation offset, the anteroposterior translation offset, and the transverse rotation offset indicated by the set of stages 130. The controller 170 can also detect a phase offset, a vertical offset, and/or a slope of the force plots. In response to a phase offset, the controller 170 can prompt the surgeon to rotate the reference surface away from the ligament reaching minimum tension before the alternative ligament to allow both ligaments to reach minimum tension simultaneously. In response to a vertical offset, the controller 170 can prompt the surgeon to translate the reference surface along the medial-lateral axis away from the ligament reaching a higher minimum tension than the alternative ligament to allow both ligaments to reach similar (e.g., equal, approximately equal) minimum tensions. In response to a slope of a force plot falling outside of a target range (e.g., increased steepness; flat curve), the controller 170 can prompt the surgeon to translate the reference surface along the anteroposterior axis, allowing the speed of the medial-collateral ligament and the speed of the lateral-collateral ligament to converge on a target (e.g., equal, approximately equal) speed.

7. Actuators

In one variation, the system 100 can further include: a set of actuators 180 and a controller 170. The set of actuators 180 includes: a first actuator 181 coupled to a first stage 131, in the set of stages 130, and configured to linearly translate the first stage 131, relative to the base 110, along a medial-lateral axis; a second actuator 182 coupled to a second stage 132, in the set of stages 130, and configured to linearly translate the second stage 132, relative to the base 110, along an anteroposterior axis; and a third actuator 183 coupled to a third stage 133, in the set of stages 130, and configured to rotate the third stage 133, relative to the base 110, about a transverse axis. The controller 170 is configured: to trigger the set of actuators 180 to oscillate the set of stages 130 to overcome static friction between the set of stages 130; and to release the set of stages 130 to relocate to positions that yield minimum compressive forces on the knee ranging tool 101 during articulation of the knee.

For example, the controller 170 can be configured: to trigger the set of actuators 180 to oscillate the set of stages 130, with diminishing displacement forces, to drive the set of stages 130 to positions that yield minimum compressive forces on the knee ranging tool 101 during articulation of the knee; and to trigger the set of actuators 180 to selectively lock the set of stages 130 responsive to entry into positions that yield minimum compressive forces on the knee ranging tool 101 during articulation of the knee.

8. Automatic Tool Centering

In a similar variation, the system 100 further includes a first force sensor, a second force sensor, a first actuator 181, and a controller 170. The first force sensor is: coupled to the set of stages 130; and configured to output a first series of force values representing tension on a medial-collateral ligament of the knee. The second force sensor is: coupled to the set of stages 130; and configured to output a second series of force values representing tension on a lateral-collateral ligament of the knee. The first actuator 181 is configured to translate a first stage 131, in the set of stages 130, along a medial-lateral axis. The controller 170 is configured: to generate a medial force versus time plot, representing tensile forces on the medial-collateral ligament over time during articulation of the knee, based on the first series of force values; to generate a lateral force versus time plot, representing tensile forces on the lateral-collateral ligament over time during articulate of the knee, based on the second series of force values; and to trigger the first actuator 181 to translate the first stage 131 along the medial-lateral axis of the knee to offset the reference surface relative to the tibia in response to detecting a vertical offset between the medial force versus time plot and the lateral force versus time plot.

In this variation, the system can also include: a second actuator 182 configured to translate a second stage 132, in the set of stages 130, along an anteroposterior axis; and a third actuator 183 configured to rotate a third stage 133, in the set of stages 130, about a transverse axis. In this variation, the controller 170 is further configured: to derive a slope of the medial force versus time plot; to trigger the second actuator 182 to translate the second stage 132 along the anteroposterior axis of the knee to offset the reference surface relative to the tibia in response to the slope of the medial force-versus-time plot falling outside of a target slope range; and to trigger the third actuator 183 to rotate the third stage 133 above the transverse axis of the knee to rotate the reference surface relative to the tibia in response to detecting a phase offset between the medial force-versus-time plot and the lateral-force-versus time plot.

As described herein, the system can include actuators configured to automatically arrange the set of stages in positions that yield minimum and/or balances medial and lateral compressive forces on the knee ranging tool 101 (and therefore minimum and/or balanced tensions on the medial and lateral ligaments of the knee) during articulation of the knee. Additionally or alternatively, the system can implement a set of springs and/or a set of magnets that cooperate to resist displacement of the stages (e.g., by controlling or increasing friction between these stages) during articulation of the knee. For example, the system can further include a set of springs: located on (e.g., bolted or screwed into) the set of stages, such as between the base and the first stage, between the second stage and the third stage, and between the third stage and the tibial reference surface; compressing adjacent stages and increasing stiction and friction between adjacent stages; and configured to constrain motion between adjacent stages during articulation of the knee. Therefore, the set of springs can control tension between the stages and enable the set of stages to slip into and remain in a location corresponding to lowest and/or balanced ligament tension as the knee is articulated. Additionally or alternatively, the system can further include a set of magnets arranged within the set of stages and/or the base in order to increase static and/or kinetic friction between the set of stages and the base.

As a person skilled in the art will recognize from the previous detailed description and from the figures and claims, modifications and changes can be made to the embodiments of the invention without departing from the scope of this invention as defined in the following claims.

I claim:
1. A system comprising:
a knee ranging tool:
    comprising a base configured to transiently locate on a resected proximal face of a tibia in a knee of a patient;

defining a tibial reference surface configured to:

run against a femoral surface of an artificial femoral component, installed on a distal face of a femur of the patient, during articulation of the knee of patient; and transiently install on a set of stages;

comprising the set of stages:

interposed between the base and the tibial reference surface;

configured to locate the tibial reference surface relative to the base; and compliant to medial-lateral translation, anteroposterior translation, and transverse rotation; and configured to indicate a medial-lateral translation offset, an anteroposterior translation offset, and a transverse rotation offset corresponding to a position of the tibial reference surface, relative to the base, that yields elastic deformation of ligaments in the knee over a range of motion of the knee; and configured to lock at a position corresponding to the medial-lateral translation offset and the anteroposterior translation offset; and a reaming guide configured to transiently install on the set of stages, in replacement of the tibial reference surface, to locate a tibial reamer during drilling of the tibia to receive a keel of an artificial tibial component.

2. The system of claim 1, further comprising:

a medial force sensor;

coupled to the set of stages; and configured to output a first series of medial force values representing tension on a medial ligament of the knee;

a lateral force sensor;

coupled to the set of stages;

laterally offset from the medial force sensor; and configured to output a second series of lateral force values representing tension on a lateral ligament of the knee; and a controller configured to:

characterize a difference between concurrent tensions on the medial ligament and tensions on the lateral ligament based on the first series of medial force values and the second first series of lateral force values;

scan the first series of medial force values for a first indication of inelastic deformation of the medial ligament; and in response to convergence of the first series of medial force values and the second series of lateral force values toward minimum forces during articulation of the knee:

in response to the difference exceeding a threshold difference:

generate a first prompt to adjust a medial-lateral position of the artificial femoral component on the distal face of the femur; and in response to absence of the first indication of inelastic deformation of the medial ligament in the first series of medial force values:

generate a second prompt to locate an artificial tibial component on the tibia according to the medial-lateral translation offset, the anteroposterior translation offset, and the transverse rotation offset indicated by the set of stages.

3. The system of claim 2, wherein the controller is further configured to:

in response to presence of the first indication of inelastic deformation of the medial ligament in the first series of medial force values:

generate a third prompt to adjust the set of stages to displace the tibial reference surface, relative to the base, toward the lateral ligament; and in response to absence of convergence of the first series of medial force values and the second series of lateral force values toward minimum forces during articulation of the knee:

generate a fourth prompt to adjust the set of stages to reposition the tibial reference surface on the base.

4. The system of claim 1:

further comprising a first keel:

extending from a distal face of the base;

defining a geometry approximating a second keel of an artificial tibial component, the artificial tibial component defining an artificial tibial surface; and configured to:

insert into a reamed bore in the tibia; and locate the base relative to the reamed bore in the tibia; and wherein the set of stages are configured to indicate:

the anteroposterior translation offset that corresponds to an anteroposterior position of the artificial tibial surface relative to the second keel on the artificial tibial component;

the medial-lateral translation offset that corresponds to a medial-lateral position of the artificial tibial surface relative to the second keel on the artificial tibial component; and the transverse rotation offset that corresponds to a transverse position of the artificial tibial surface relative to the second keel on the artificial tibial component.

5. The system of claim 1:

wherein the base is configured to locate on the resected face of the tibia via a set of laterally offset pins; and further comprising a tibial reaming tool comprising:

a second base configured to transiently locate on the resected proximal face of the tibia via the set of pins;

a reaming guide configured to locate a tibial reamer during drilling of the tibia to receive a keel of an artificial tibial component; and a second set of stages:

interposed between the base and the tibial reference surface; and configured to adjust in medial-lateral translation and anteroposterior translation according to the medial-lateral translation offset and the anteroposterior translation offset.

6. The system of claim 1, further comprising:

a first force sensor:

coupled to the set of stages; and configured to output a first series of force values representing tension on a medial-collateral ligament of the knee;

a second force sensor:

coupled to the set of stages; and configured to output a second series of force values representing tension on a lateral-collateral ligament of the knee; and a controller configured to:

generate a medial force-versus-time plot, representing tensile forces on the medial-collateral ligament over time during articulate of the knee, based on the first series of force values;

generate a lateral force-versus-time plot, representing tensile forces on the lateral-collateral ligament over time during articulate of the knee, based on the second series of force values; and in response to the medial force versus time plot approximating the lateral force-versus-time time plot:

generate a first prompt to locate an artificial tibial component on the tibia according to the medial-lateral translation offset, the anteroposterior translation offset, and the transverse rotation offset indicated by the set of stages.

7. The system of claim 6, wherein the controller is further configured to:

in response to detecting a phase offset between the medial force-versus-time plot and the lateral force-versus-time plot:

generate a second prompt to rotate the reference surface about a transverse axis of the knee via the set of stages;

in response to detecting a vertical offset between the medial force-versus-time plot and the lateral force-versus-time plot:

generate a third prompt to translate the reference surface along a medial-lateral axis of the knee via the set of stages;

derive a slope of the medial force-versus-time plot; and in response to the slope of the medial force-versus-time plot falling outside of a target slope range:

generate a fourth prompt to translate the reference surface, along a anteroposterior axis of the knee via the set of stages.

8. The system of claim 1, further comprising:

a first force sensor:

coupled to the set of stages; and configured to output a first series of force values representing tension on a medial-collateral ligament of the knee;

a second force sensor:

coupled to the set of stages; and configured to output a second series of force values representing tension on a lateral-collateral ligament of the knee;

a first actuator configured to translate a first stage, in the set of stages, along a medial-lateral axis; and a controller configured to:

generate a medial force-versus-time plot, representing tensile forces on the medial-collateral ligament over time during articulate of the knee, based on the first series of force values;

generate a lateral force-versus-time plot, representing tensile forces on the lateral-collateral ligament over time during articulate of the knee, based on the second series of force values; and in response to detecting a vertical offset between the medial force-versus-time plot and the lateral force-versus-time plot:

trigger the first actuator to translate the first stage along the medial-lateral axis of the knee to offset the reference surface relative to the tibia.

9. The system of claim 8:

further comprising:

a second actuator configured to translate a second stage, in the set of stages, along an anteroposterior axis;

a third actuator configured to rotate a third stage, in the set of stages, about a transverse axis; and wherein the controller is configured to:

derive a slope of the medial force versus time plot; and in response to the slope of the medial force versus time plot falling outside of a target slope range:

trigger the second actuator to translate the second stage along the anteroposterior axis of the knee to offset the reference surface relative to the tibia; and in response to detecting a phase offset between the medial force versus time plot and the lateral force versus time plot:

trigger the third actuator to rotate the third stage above the transverse axis of the knee to rotate the reference surface relative to the tibia.

10. The system of claim 1, further comprising:

a set of actuators comprising:

a first actuator coupled to a first stage, in the set of stages, and configured to linearly translate the first stage, relative to the base, along a medial-lateral axis;

a second actuator coupled to a second stage, in the set of stages, and configured to linearly translate the second stage, relative to the base, along an anteroposterior axis; and a third actuator coupled to a third stage, in the set of stages, and configured to rotate the third stage, relative to the base, about a transverse axis; and a controller configured to:

trigger the set of actuators to oscillate the set of stages to overcome static friction between the set of stages; and release the set of stages to relocate to positions that yield minimum compressive forces on the knee ranging tool during articulation of the knee.

11. The system of claim 1, further comprising:

a set of actuators comprising:

a first actuator coupled to a first stage, in the set of stages, and configured to linearly translate the first stage, relative to the base, along a medial-lateral axis;

a second actuator coupled to a second stage, in the set of stages, and configured to linearly translate the second stage, relative to the base, along an anteroposterior axis; and a third actuator coupled to a third stage, in the set of stages, and configured to rotate the third stage, relative to the base, about a transverse axis; and a controller configured to:

trigger the set of actuators to oscillate the set of stages, with diminishing displacement forces, to drive the set of stages to positions that yield minimum compressive forces on the knee ranging tool during articulation of the knee; and trigger the set of actuators to selectively lock the set of stages responsive to entry into positions that yield minimum compressive forces on the knee ranging tool during articulation of the knee.

12. The system of claim 9:

further comprising a set of position sensors, each position sensor in the set of position sensors configured to output a position of a stage in the set of stages; and wherein the controller is configured to:

reduce the force output of the set of actuators during sequential articulations of the knee; and implement a closed-loop control to maintain a first stage in the set of stages at a first position in response to the first position approximating a lowest-energy position of the stage in the set of stages.

13. A system comprising:

a knee ranging tool:

comprising a base configured to transiently locate on a resected proximal face of a tibia in a knee of a patient;

defining a tibial reference surface configured to run against a femoral surface of an artificial femoral component, installed on a distal face of a femur of the patient, during articulation of the knee of patient;

comprising a set of stages:

interposed between the base and the tibial reference surface;

configured to locate the tibial reference surface relative to the base; and compliant to medial-lateral translation, anteroposterior translation, and transverse rotation; and configured to indicate a medial-lateral translation offset and an anteroposterior translation offset corresponding to a position of the tibial reference surface, relative to the base, that yields elastic deformation of ligaments in the knee over a range of motion of the knee; and a reaming guide:

configured to transiently install on the tibia;

adjustable over a range of medial-lateral translation, and anteroposterior positions; and configured to locate a tibial reamer, during drilling of the tibia to receive a keel of an artificial tibial component, according to the medial-lateral translation offset and the anteroposterior translation offset.

14. A system comprising:

a knee ranging tool:

comprising a base configured to transiently locate on a resected proximal face of a tibia in a knee of a patient;

defining a tibial reference surface configured to run against a femoral surface of an artificial femoral component, installed on a distal face of a femur of the patient, during articulation of the knee of patient;

comprising a set of stages:

interposed between the base and the tibial reference surface;

configured to locate the tibial reference surface relative to the base; and comprising:

a first stage compliant in medial-lateral translation and configured to translate along a medial-lateral axis responsive to a first force component, along the medial-lateral axis, of a combined force applied by a medial-collateral ligament and a lateral-collateral ligament of the knee to the artificial femoral component and the tibia during articulation of the knee;

a second stage compliant in anteroposterior translation and configured to translate along an anteroposterior axis responsive to a second force component, along the anteroposterior axis, of the combined force applied by the medial-collateral ligament and the lateral-collateral ligament during articulation of the knee; and a third stage compliant in transverse rotation and configured to rotate about a transverse axis responsive to a torque, above the transverse axis, resulting from the combined force applied by the medial-collateral ligament and the lateral-collateral ligament during articulation of the knee; and configured to indicate a medial-lateral translation offset, an anteroposterior translation offset, and a transverse rotation offset corresponding to a position of the tibial reference surface, relative to the base, that yields elastic deformation of ligaments in the knee over a range of motion of the knee.

15. A system comprising:

a knee ranging tool:

comprising a base configured to transiently locate on a resected proximal face of a tibia in a knee of a patient;

defining a tibial reference surface configured to run against a femoral surface of an artificial femoral component, installed on a distal face of a femur of the patient, during articulation of the knee of patient;

comprising:

a set of stages:

interposed between the base and the tibial reference surface;

compliant to medial-lateral translation, anteroposterior translation, and transverse rotation;

comprising manually operable set position controls; and configured to:

locate the tibial reference surface relative to the base;

translate in response to surgeon input during surgery;

transiently lock in place in response to surgeon input during surgery during articulation of the knee through a range of motion; and transiently unlock, in response to surgeon input, in response to force sensor output deviating from a target force in the range of motion indicating a balanced and elastic position of the tibial reference surface with respect to the artificial femoral component; and a medial force sensor:

coupled to the set of stages; and configured to output a first series of medial force values representing tension on a medial ligament of the knee; and a lateral force sensor:

coupled to the set of stages;

laterally offset from the medial force sensor; and configured to output a second series of lateral force values representing tension on a lateral ligament of the knee; and configured to indicate a medial-lateral translation offset, an anteroposterior translation offset, and a transverse rotation offset corresponding to a position of the tibial reference surface, relative to the base, that yields elastic deformation of ligaments in the knee over the range of motion of the knee based on the first series of medial force values and the second series of lateral force values.

16. A system comprising:

a knee ranging tool:

comprising a base configured to transiently locate on a resected proximal face of a tibia in a knee of a patient;

defining a tibial reference surface configured to run against a femoral surface of an artificial femoral component, installed on a distal face of a femur of the patient, during articulation of the knee of patient; comprising a set of stages:

interposed between the base and the tibial reference surface;

configured to locate the tibial reference surface relative to the base; and compliant to medial-lateral translation, anteroposterior translation, and transverse rotation; and configured to indicate a medial-lateral translation offset, an anteroposterior translation offset, and a transverse rotation offset corresponding to a position of the tibial reference surface, relative to the base, that yields elastic deformation of ligaments in the knee over a range of motion of the knee;

a set of position sensors, each position sensor in the set of position sensors configured to detect a position of a stage in the set of stages; and a controller configured to:

read the position of the stage from the position sensor; and output:

a medial-lateral position in the coronal plane of a first stage;

an anteroposterior position in the sagittal of a second stage; and a rotational position in the transverse plane of a third stage.

17. A system comprising:

a knee ranging tool:

comprising a base configured to transiently locate on a resected proximal face of a tibia in a knee of a patient;

defining a tibial reference surface configured to run against a femoral surface of an artificial femoral component, installed on a distal face of a femur of the patient, during articulation of the knee of patient comprising a set of stages:

interposed between the base and the tibial reference surface;

configured to locate the tibial reference surface relative to the base; and compliant to medial-lateral translation, anteroposterior translation, and transverse rotation; and comprising a set of indicators:

comprising:

a first set of linear rule demarcations between a first stage and the base;

a second set of linear rule demarcations between a second stage and the first stage; and a third set of angular rule demarcations between a third stage and the second stage; and configured to indicate a medial-lateral translation offset, an anteroposterior translation offset, and a transverse rotation offset corresponding to a position of the tibial reference surface, relative to the base, that yields elastic deformation of ligaments in the knee over a range of motion of the knee.

18. A system comprising:

a knee ranging tool:

comprising a base configured to transiently locate on a resected proximal face of a tibia in a knee of a patient;

defining a tibial reference surface:

configured to run against a femoral surface of an artificial femoral component, installed on a distal face of a femur of the patient, during articulation of the knee of patient; and approximating a geometry of a condyle of an artificial tibial component selected for installation on the tibia of the patient;

comprising a set of stages:

interposed between the base and the tibial reference surface;

configured to locate the tibial reference surface relative to the base; and compliant to medial-lateral translation, anteroposterior translation, and transverse rotation; and configured to indicate a medial-lateral translation offset, an anteroposterior translation offset, and a transverse rotation offset corresponding to a position of the tibial reference surface, relative to the base, that yields elastic deformation of ligaments in the knee over a range of motion of the knee.

19. A system comprising:

a knee ranging tool:

comprising a base configured to transiently locate on a resected proximal face of a tibia in a knee of a patient;

defining a tibial reference surface:

configured to run against a femoral surface of an artificial femoral component, installed on a distal face of a femur of the patient, during articulation of the knee of patient; and comprising a set of grooves configured to run along a set of condyles of the artificial femoral component during articulation of the knee;

comprising a set of stages:

interposed between the base and the tibial reference surface;

configured to locate the tibial reference surface relative to the base; and compliant to medial-lateral translation, anteroposterior translation, and transverse rotation; and configured to indicate a medial-lateral translation offset, an anteroposterior translation offset, and a transverse rotation offset corresponding to a position of the tibial reference surface, relative to the base, that yields elastic deformation of ligaments in the knee over a range of motion of the knee.

* * * * *